US008796482B2

(12) United States Patent
Neumann et al.

(10) Patent No.: US 8,796,482 B2
(45) Date of Patent: Aug. 5, 2014

(54) OXIDATION OF PRIMARY ALIPHATIC ALCOHOLS WITH A NOBLE METAL POLYOXOMETALATE COMPLEX

(75) Inventors: Ronny Neumann, Kfar-Saba (IL); Delina Barats, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 255 days.

(21) Appl. No.: 13/499,715

(22) PCT Filed: Sep. 19, 2010

(86) PCT No.: PCT/IL2010/000770
§ 371 (c)(1),
(2), (4) Date: Apr. 2, 2012

(87) PCT Pub. No.: WO2011/039744
PCT Pub. Date: Apr. 7, 2011

(65) Prior Publication Data
US 2012/0197033 A1    Aug. 2, 2012

Related U.S. Application Data

(60) Provisional application No. 61/272,506, filed on Oct. 1, 2009.

(51) Int. Cl.
C07F 19/00    (2006.01)
C07C 45/38    (2006.01)
C07C 45/29    (2006.01)
C07F 15/00    (2006.01)
C07F 11/00    (2006.01)
B01J 23/652   (2006.01)

(52) U.S. Cl.
CPC ............... *C07F 11/005* (2013.01); *C07C 45/29* (2013.01); *C07F 15/0066* (2013.01); *C07C 45/38* (2013.01); *B01J 23/6527* (2013.01)
USPC .................. 556/28; 556/43; 556/51; 568/471

(58) Field of Classification Search
CPC ............................... C07C 45/38; C07F 19/005
USPC .................................. 556/28, 43, 51; 568/471
See application file for complete search history.

(56) References Cited

U.S. PATENT DOCUMENTS

2004/0192972 A1    9/2004    Choudhary et al.

FOREIGN PATENT DOCUMENTS

| WO | WO 98/54165 | 12/1998 |
|----|-------------|---------|
| WO | WO 03/053556 | 7/2003 |
| WO | WO 2007/139616 | 12/2007 |
| WO | WO 2008/128638 | 10/2008 |
| WO | WO 2011/039744 | 4/2011 |

OTHER PUBLICATIONS

Translation of Office Action Dated Jun. 26, 2013 From the State intellectual Property Office of the People's Republic of China Re. Application No. 201080044557.5.
Translation of Search Report Dated Jun. 18, 2013 From the State Intellectual Property Office of the People's Republic of China Re. Application No. 201080044557.5.

(Continued)

*Primary Examiner* — Porfirio Nazario Gonzalez (57) ABSTRACT

A process of oxidizing primary alcohols to their corresponding aldehydes is disclosed. The process is effected in the presence of noble metal polyoxometalate complexes. A novel process for preparing noble metal polyoxometalate complexes, and novel noble metal polyoxometalate complexes are also disclosed.

37 Claims, 2 Drawing Sheets
(1 of 2 Drawing Sheet(s) Filed in Color)

(56) References Cited

OTHER PUBLICATIONS

International Preliminary Report on Patentability Dated Apr. 12, 2012 From the International Bureau of WIPO Re. Application No. PCT/IL2010/000770.

Communication Relating to the Results of the Partial International Search Dated Aug. 25, 2011 From the International Searching Authority Re: Application No. PCT/IL2010/000770.

International Search Report and the Written Opinion Dated Nov. 2, 2011 From the international Searching Authority Re: Application No. PCT/IL2010/000770.

Choudary et al. "Catalytic Properties of Several Palladium Complexes Covalently Anchored Onto Silica for the Aerobic Oxidation of Alcohols", Green Chemistry, 8: 479-482, 2006.

Jensen et al. "A Well-Defined Complex for Palladium-Catalyzed Aerobic Oxidation of Alcohols: Design, Synthesis, and Mechanistic Considerations", Angewandte Chemie International Edition, 42(32): 3810-3813, 2003.

Mizuno Abstract, Claims 1, 5, 6, 7, 11, 12, Ex.20, Compound Catalyst A.

Neumann et al. "A Ruthenium-Substituted Polyoxometalate as an Inorganic Dioxygenase for Activation of Molecular Oxygen", Nature, XP009113239, 388(6640): 353-355, 1997. Abstract, p. 353, col. 1, Last Para—col. 2, Para 1, Fig.1.

Neumann et al. "Molecular Oxygen Activation by a Ruthenium-Substituted 'Sandwich' Type Polyoxometalate", Journal of the American Chemical Society, XP009113238, 120(46): 11969-11976, Nov. 25, 1998. Abstract, p. 11972, col. 2, Fig.5, p. 11975, col. 2, Last Para.

Neumann et al. "Noble-Metal (RuIII, PdII, PtII) Substituted 'Sandwich' Type Polyoxometalates: Preparation, Characterization, and Catalytic Activity in Oxidations of Alkanes and Alkenes by Peroxides", Inorganic Chemistry, XP007907528, 34(23): 5753-5760, Nov. 1995. Abstract, p. 5755, p. 5759, Table 4.

Nishimura et al. "Palladium(II)-Catalyzed Oxidation of Alcohols to Aldehydes and Ketones by Molecular Oxygen", Journal of Organic Chemistry, 64(18): 6750-6755, 1999.

Nishimura et al. "Pd(OAc)2-Catalyzed Oxidation of Alcohols to Aldehydes and Ketones by Molecular Oxygen", Tetrahedron Letters, XP004126786, 39(33): 6011-6014, Aug. 13, 1998. p. 6013, Table 2.

Nomiya et al. "Synthesis and Characterization of a Monoruthenium(III)-Substituted Dawson Polyoxotungstate Derived by Br2 Oxidation of the 1:2 Complex of Ruthenium(II) and [Alpha2-P2W17O61]10-. The Reactivity of Cis—[RuCl2(DMSO)4] as a Ruthenium Source", Journal of the Chemical Society, Dalton Transactions, XP009113232, 9: 1506-1512, May 7, 2001. Abstract, p. 1507, col. 1.

Pillai et al. "Selective Oxidation of Alcohols by Molecular Oxygen Over a Pd/MgO Catalyst in the Absence of Any Additives", Green Chemistry, XP009151300, 6(3): 161-165, 2004. p. 163, Table 3.

Price et al. "Palladium(II) and Platinum(II) Alkyl Sulfoxide Complexes. Examples of Sulfur-Bonded, Mixed Sulfur- and Oxygen-Bonded, and Totally Oxygen-Bonded Complexes", Inorganic Chemistry, 11(6): 1280-1284, 1972.

Rong et al. "Lacunary Polyoxometalate Anions Arc Pi-Acceptor Ligands. Characterization of Some Tungstoruthenate(II,III,IV,V) Heteropolyanions and Their Atom-Transfer Reactivity", Journal of the American Chemical Society, XP007907529, 114(8): 2932-2938, Jan. 1, 1992. p. 2937, col. 1, Last Para.

Tourne et al. "Chiral Polytungstometalates [WM3(H2O)2(XW9O34)2]12-(X=M=Zn or CoII) and Their M-Substituted Derivatives. Syntheses, Chemical, Structural and Spectroscopic Study of Some D,L Sodium and Potassium Salts", Journal of the Chemical Society, Dalton Transactions, XP009151302, p. 143-155, 1991. p. 152, Table 6, p. 153, col. 1, Last Para.

Weiner et al. "An All-Inorganic, Polyoxometalate-Based Catechol Dioxygenase That Exhibits > 100 000 Catalytic Turnovers", Journal of the American Chemical Society, XP055004919, 121(42): 9831-9842, Oct. 1, 1999. p. 9835, Table 1, Compound X.

OXIDATION OF PRIMARY ALIPHATIC ALCOHOLS WITH A NOBLE METAL POLYOXOMETALATE COMPLEX

RELATED APPLICATIONS

This application is a National Phase of PCT Patent Application No. PCT/IL2010/000770 having International filing date of Sep. 19, 2010, which claims the benefit of priority of U.S. Provisional Patent Application No. 61/272,506 filed on Oct. 1, 2009. The contents of the above applications are all incorporated herein by reference.

FIELD AND BACKGROUND OF THE INVENTION

The present invention, in some embodiments thereof, relates to the field of chemistry, and more particularly, but not exclusively, to novel processes for oxidation of alcohols to aldehydes, to noble metal-polyoxometalate complex catalysts (NM-POM) such as palladium(II)-polyoxometalate complexes (Pd-POM) for use in these processes and to methods of preparing these complexes.

The catalytic oxidation of alcohols using ground state molecular oxygen, $O_2$, as a primary oxidant, has concentrated many efforts in recent years, and attracted many researchers expressly motivated by the apparent ecological advantage that such a transformation would have, compared to other methods.

There are three general rules of thumb that may be used when describing the reactivity and selectivity in these oxidation reactions: i) benzylic alcohols are the most reactive substrates, allylic alcohols have intermediate reactivity and saturated aliphatic alcohols are the least reactive; ii) typically secondary alcohols are more reactive than primary alcohols; and iii) while oxidation of secondary alcohols is typically selective to ketones, the selective oxidation primary (non-benzylic) alcohols to aldehydes is more difficult and over-oxidation to carboxylic acids is not uncommon.

In the context of selective oxidation of primary aliphatic alcohols to the corresponding aldehydes, there are some notable examples of catalysts that are selective for this transformation, which also clearly show specificity for primary versus secondary alcohols. Some of the most studied systems are those that combine metal catalysts with nitroxyl radicals, typically 2,2,6,6-tetramethylpiperidine-1-oxyl (TEMPO), as co-catalysts. In these catalytic systems an in situ formed nitrosonium cation oxidizes alcohols to aldehydes and the hydroxylamine formed is re-oxidized by $O_2$ in the presence of an additional metal catalyst. Other examples include a $Cu^{II}$-iminosemiquinone catalyst that oxidizes primary alcohols to aldehydes with formation of $H_2O_2$ and with which secondary alcohols do not react, co-catalytic systems comprised of $Ru(PPh_3)_3Cl_2$/hydroquinone, water-soluble diruthenium complexes, nitrosylruthenium-salen catalysts with photo-irradiation, Os—Cr and Ru—Cr heterobimetallic complexes, and Au—Pd supported on $TiO_2$, although the results obtained for the latter are equivocal since 3-octanol was as reactive as 1-octanol, but 2-octanol was not reactive.

A very significant portion of the research in the area of aerobic oxidation of alcohols has been directed at the use of noble metals, and in particular at the use of palladium (Pd) complexes as well as Pd colloids as catalyst in homogeneous and heterogeneous reaction systems.

A proposed mechanism of palladium(II)-catalyzed oxidations of alcohols in the presence of $O_2$ is illustrated in Scheme 1 below, wherein B denotes a base, L denotes a metal-complexing ligand and R and R' denote, for example, different alkyl residues.

Scheme 1

The mechanism presented in Scheme 1 above, is generally thought to involve (a) the ligation of the alcohol by reaction of the conjugate alkoxide with the transition metal, followed by (b) β-elimination to yield the carbonyl (ketone or aldehyde) product and a two electron reduced Pd(0) and/or Pd(II)-H complex. The rate determining step is often (c) the $O_2$ dependent re-oxidation step, and involves the intermediate formation of $H_2O_2$, which is typically decomposed by disproportionation. Notably, basic conditions are beneficial for formation of alkoxides and therefore to initiate the catalytic cycle.

In general, palladium-based oxidation catalysts suffer from instability and rapidly degrading aptitude for regeneration for repetitive use, and in addition are expensive. Attempts to stabilize palladium catalysts included fixation to polymers (also referred to as Pd-support) and complexation with various ligands. These attempts were also directed at achieving some degree of selectivity and control in the oxidation reaction with respect to the reacting species and the end products of these reactions. However, although there are isolated examples of oxidation of aliphatic primary alcohols to corresponding aldehydes (see, for example, Nishimura, T. et al., *Tetrahedron Lett.* 1998, 39, 6011-6014; Nishimura, T. et al., *J. Org. Chem.* 1999, 64, 6750-6755; Jensen, D. R. et al., *Angew. Chem. Int. Ed.* 2003, 42, 3810-3813; Choudary, D. et al.,

*Green Chem.* 2006, 8, 479-482; and Pillai, U. R. et al., *Green Chem.* 2004, 6, 161-165), there are no reports hitherto which describe selective oxidation of primary over secondary aliphatic alcohols coupled with selective formation of aldehydes, afforded by catalytic oxidation using palladium-based catalysts.

U.S. Pat. Nos. 6,229,028, 6,573,394 and 6,762,310 teach processes for the catalytic epoxidation of alkenes using transition metal (e.g., ruthenium, nickel, cobalt and molybdenum) substituted polyoxofluorometalate complexes in the presence of molecular oxygen.

Palladium (Pd) polyoxometalate complexes such as the compounds $Q_{12}\{[WZnPd_2(H_2O)_2](ZnW_9O_{34})_2\}$ wherein Q is Na or K and the compound $Q_{12}\{[WZnPd_2(H_2O)_2](ZnW_9O_{34})_2\}$ wherein Q is a quaternary ammonium salt were disclosed by Tourné, C. M. et al. in *J. Chem. Soc., Dalton Trans.* 1991, 143-155; and in Neumann, R., et al., *Inorganic Chemistry*, 1995, 34, 5753-5360, respectively.

SUMMARY OF THE INVENTION

The present invention, in some embodiments thereof, relates to the field of chemistry, and more particularly, but not exclusively, to novel processes for oxidation of alcohols to aldehydes, to noble metal-polyoxometalate complex catalysts (NM-POM) such as palladium(II)-polyoxometalate complexes (Pd-POM) for use in these processes and to methods of preparing these complexes.

According to an aspect of embodiments of the invention there is provided a process of oxidizing a primary alcohol to a corresponding aldehyde, the process comprising mixing the primary alcohol with a noble metal-polyoxometalate complex (NM-POM), thereby obtaining the aldehyde.

In some embodiments, the aldehyde constitutes at least 80, 85 or 90 mol percents of the products obtained upon the mixing.

In some embodiments, the aldehyde constitutes at least 95 mol percents of the products obtained upon the mixing.

In some embodiments, mixing the reactants is performed in an organic solvent.

In some embodiments, mixing the reactants is performed in the presence of a catalytic amount of the NM-POM.

In some embodiments, mixing the reactants is effected in an atmosphere having an $O_2$ partial pressure.

In some embodiments, the $O_2$ partial pressure ranges from 0.1 bar to about 5 bar.

In some embodiments, mixing the reactants is effected in the absence of $O_2$.

In some embodiments, mixing the reactants is performed in the presence of a non-catalytic amount of the NM-POM.

In some embodiments, mixing the reactants is effected at a temperature that ranges from about 80° C. to about 140° C.

In some embodiments, the primary alcohol is selected from the group consisting of a saturated or unsaturated, substituted or unsubstituted aliphatic alcohol, a saturated or unsaturated, substituted or unsubstituted alicyclic alcohol, a saturated or unsaturated, substituted or unsubstituted heteroalicyclic alcohol, a substituted or unsubstituted aromatic alcohol and a substituted or unsubstituted heteroaromatic alcohol.

In some embodiments, the noble metal-polyoxometalate complex (NM-POM) has a general Formula I:

Formula I and any solvate or hydrate thereof, wherein:

X is a heteroatom selected from the group consisting of a main group element, H, alkali metal, alkaline earth metal, a transition metal or any combination thereof;

a is 0 or an integer from 1 to 6;

NM is a noble metal selected from the group consisting of palladium, ruthenium, rhodium, silver, osmium, iridium, platinum and gold;

d is an integer from 1 to 10;

L is a ligand selected from the group consisting of $H_2O$, halide, oxygen, hydroxyl, DMSO, sulphoxide, cyanide, cyanate, thiocyanate, amine, heteroaryl, heteroalicyclic and any combination thereof;

g an integer from 1 to 10;

M is selected from the group consisting of tungsten (W), molybdenum (Mo), niobium (Nb) or vanadium (V) or any combination thereof;

m is an integer from 4 to 100;

O is oxygen;

z in an integer from 5 to 400;

Q is a counter-cation selected from the group consisting of an alkali metal cation, an alkaline earth metal cation, a transition metal cation, an organic cation, a substituted or unsubstituted quaternary ammonium cation, a phosphonium cation, an arsenium cation and any combination thereof; and q is an integer from 1 to 100.

In some embodiments, the noble metal (NM) is palladium, and in some embodiments, d is 2.

In some embodiments, the quaternary ammonium cation has a general Formula II:

$$(R_1R_2R_3R_4)N^+ \qquad \text{Formula II}$$

wherein each of $R_1$, $R_2$, $R_3$ and $R_4$ is independently selected from the group consisting of hydrogen, alkyl, alkenyl, cycloalkyl, heteroalicyclic, aryl and heteroaryl.

In some embodiments, $R_1$ is an alkyl having from 4 to 20 carbon atoms.

In some embodiments, $R_2$, $R_3$ and $R_4$ are each independently an alkyl having from 1 to 4 carbon atoms.

In some embodiments, the quaternary ammonium cation is $C_{16}H_{33}(CH_3)_3N^+$.

In some embodiments, X is selected from the group consisting of Zn, Co, P, B, As, Ge, Si, Bi, Al, Sn and Sb In some embodiments, M is selected from the group consisting of W, Mo and V.

In some embodiments, L is $H_2O$.

In some embodiments, the noble metal-polyoxometalate complex is $(C_{16}H_{33}(CH_3)_3N^+)_{12}[Zn_3Pd_2(H_2O)_2W_{19}O_{68}]$.

According to another aspect of the present invention, there is provided a process of preparing a noble metal-polyoxometalate complex (NM-POM) having a general Formula I:

Formula I and any solvate or hydrate thereof, wherein:

X is selected from the group consisting of a main group element, H, alkali metal, alkaline earth metal, a transition metal or any combination thereof;

a is 0 or an integer from 1 to 6;

NM is a noble metal selected from the group consisting of palladium, ruthenium, rhodium, silver, osmium, iridium, platinum and gold;

d is an integer from 1 to 10;

L is a ligand selected from the group consisting of $H_2O$, halide, oxygen, hydroxyl, DMSO, sulphoxide, cyanide, cyanate, thiocyanate, amine, heteroaryl, heteroalicyclic and any combination thereof;

g an integer from 1 to 10;

M is selected from the group consisting of tungsten (W), molybdenum (Mo), niobium (Nb) or vanadium (V) or any combination thereof;

m is an integer from 4 to 100;

O is oxygen;

z in an integer from 5 to 400;

Q is a counter-cation selected from the group consisting of an alkali metal cation, an alkaline earth metal cation, a transition metal cation, an organic cation, a substituted or unsubstituted quaternary ammonium cation, a phosphonium cation, an arsenium cation and any combination thereof; and q is an integer from 1 to 100, the process is effected by:

mixing an $NM[(CH_3)_2SO]_2Cl_2$ salt with a solution of a first complex having the general formula III:

$$Q_q[X_aL_gM_mO_z]^{q-} \qquad \text{Formula III}$$

thereby obtaining the NM-POM complex.

In some embodiments, the molar ratio of $NM[(CH_3)_2SO]_2Cl_2$ to the first complex ranges from 10:1 to 1:10.

In some embodiments, the molar ratio of $NM[(CH_3)_2SO]_2Cl_2$ to the first complex ranges from 3:1 to 1:3.

In some embodiments, the ratio is 1:2.

In some embodiments, the mixing is effected by adding $NM[(CH_3)_2SO]_2Cl_2$ to the solution of the first complex.

In some embodiments, the process further includes, prior to the mixing:

reacting a second complex having the general formula IV:

$$Na_q[X_aL_gM_mO_x]^{q-} \qquad \text{Formula IV}$$

and any solvate or hydrate thereof, with a salt having the counter cation to thereby obtain the first complex having the general formula III.

In some embodiments, the counter cation is a quaternary ammonium cation having a general Formula II:

$$(R_1R_2R_3R_4)N^+ \qquad \text{Formula II}$$

wherein each of $R_1$, $R_2$, $R_3$ and $R_4$ is independently selected from the group consisting of hydrogen, alkyl, alkenyl, cycloalkyl, heteroalicyclic, aryl and heteroaryl.

In some embodiments, NM is palladium.

In some embodiments, X is selected from the group consisting of Zn, Co, P, B, As, Ge, Si, Bi, Al, Sn and Sb.

In some embodiments, M is selected from the group consisting of W, Mo and V.

In some embodiments, L is $H_2O$.

In some embodiments, the noble metal-polyoxometalate complex is $(C_{16}H_{33}(CH_3)_3N^+)_{12}[Zn_5(H_2O)_2PdCl_2W_{19}O_{68}]$.

As used herein the term "about" refers to ±10%.

The terms "comprises", "comprising", "includes", "including", "having" and their conjugates mean "including but not limited to". The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "an agent" or "at least one agent" may include a plurality of agents, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, to exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings.

DESCRIPTION OF EMBODIMENTS OF THE INVENTION

The present invention, in some embodiments thereof, relates to the field of chemistry, and more particularly, but not exclusively, to novel processes for oxidation of alcohols to aldehydes, to noble metal-polyoxometalate complex catalysts (NM-POM) such as palladium(II)-polyoxometalate complexes (Pd-POM) for use in these processes and to methods of preparing these complexes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Noble metals, such as palladium, are known as useful core catalysts since they induce various transformations in organic synthesis. The use of palladium (or other noble metals) complexes as oxidants of alcohols, however, is limited by their low selectivity towards primary alcohols versus secondary alcohols.

As discussed hereinabove, noble metal-containing polyoxometalates such as ruthenium-based substituted polyoxometalate complexes were disclosed in U.S. Pat. No. 6,229,028 as catalysts in the epoxidation of alkenes. Other noble metal-containing polyoxofluorometalate complexes were disclosed in U.S. Pat. Nos. 6,573,394 and 6,762,310, also as catalysts in the epoxidation of alkenes, in the presence of molecular oxygen.

Other transition metal-based polyoxometalate complexes have also been prepared. However, no transition/noble metal-containing polyoxometalate complexes have ever been used hitherto as catalysts for the oxidation of primary alcohol in the presence or absence of molecular oxygen.

While studying palladium-polyoxometalate complexes as a stable species, the present inventors have surprisingly uncovered that some palladium-polyoxometalate complexes can be efficiently utilized for oxidation of alcohols, and particularly in selective oxidation of primary aliphatic alcohols in reactions which yield aldehydes rather than carboxylic acids. These complexes were shown to exhibit preference and heightened reactivity towards primary aliphatic alcohols versus secondary alcohols.

An exemplary noble metal polyoxometalate complex (NM-POM) according to some embodiments of the present invention, namely, the palladium(II)-polyoxometalate complex referred to herein as Pd-POM-1 (see, FIGS. 1A-B), was obtained by reaction of one equivalent of $PdCl_2DMSO_2$ with two equivalents the hexadecyltrimethylammonium salt of "sandwich" polyoxometalate, $(C_{16}H33(CH_3)_3N^+)_{12}[Zn_5(H_2O)_2W_{19}O_{68}]$ in a $CH_2Cl_2$ solution.

Hence, according to an aspect of some embodiments of the present invention, there is provided a process of oxidizing a primary alcohol to its corresponding aldehyde, which is effected by reacting the primary alcohol with a noble metal-polyoxometalate complex (NM-POM), as defined herein.

This process is also regarded as a process of synthesizing aldehydes from their respective primary alcohols.

Polyoxometalates are oligomeric oxides of defined structure based on addenda of tungsten, molybdenum, niobium or vanadium or a combination thereof. Transition metal-containing polyoxometalates can be represented by the general formula $[X_a(TM)_dL_gM_mO_z]^{q-}$ where the heteroatom, X, if present (i.e., when a is not 0) may be, for example, main group or transition metals; the addenda atoms, M, are molybdenum, tungsten, niobium or vanadium or a combination thereof; and TM is one or several different transition metals, including noble metals. The TM atom can be any transition metal of the first, second or third row or a noble metal such as ruthenium, rhodium, palladium, osmium, iridium and/or platinum.

The noble metal (NM)-containing polyoxometalates, $[X_a(NM)_dL_gM_mO_z]^{q-}$, presented herein, are characterized as a dimer of a truncated Keggin structure having a "belt" of X (heteroatoms such as Zn), M (such as W) and other noble metal cations "sandwiched" between the two $X_aM_mO_z$ trivacant Keggin fragments the structure of which is shown in FIG. 1. Without being bound to any particular theory or supposition, the noble metal cations are assumed to be positioned at terminal positions and are hexacoordinate with at least one labile ligand such as water. The heteroatom atom, X of the trivacant Keggin fragments can be any heteroatom known for Keggin compounds as is well-known in the art. For example, X can be a nonmetal such as phosphorous, silicon germanium, boron, or arsenic. Alternatively X can be a metal such as zinc, cobalt, iron and the likes. The counter cation of the above transition metal substituted polyoxometalates may be any cation including for example alkali metals, alkaline earth cations, transition metal cations or organic cations such as quaternary ammonium salts.

According to some embodiments, noble metal polyxoxometalate complexes such as those described in U.S. Pat. Nos. 6,229,028, 6,573,394 and 6,762,310, and in Tourné C. M. et al. and in Neumann R., et al., (supra), which are all incorporated by reference as if fully set forth herein, can be utilized in the context of the present embodiments. Other noble metal polyoxometalate complexes are also contemplated.

According to some embodiments of the invention, the noble metal-polyoxometalate complexes (NM-POM) can be represented by the general Formula I:

$$Q^+_q[X_a(NM)_dL_gM_mO_z]^{q-} \qquad \text{Formula I}$$

including any solvate or hydrate thereof, wherein:

X is a heteroatom selected from the group consisting of a main group element, H, alkali metal, alkaline earth metal, a transition metal or any combination thereof;

a is 0 or an integer from 1 to 6;

NM is a noble metal;

d is an integer from 1 to 10;

L is a ligand;

g an integer from 1 to 10;

M is selected from the group consisting of tungsten (W), molybdenum (Mo), niobium (Nb) or vanadium (V) or any combination thereof;

m is an integer from 4 to 100;

O is oxygen;

z in an integer from 5 to 400;

Q is a counter-cation countering the charge $q^-$; and q is an integer from 1 to 100.

The phrase "noble metal", as used herein, encompasses a metallic element belonging to a group of metals that are resistant to corrosion and oxidation by oxygen to and water, and traditionally include, in order of increasing atomic number, ruthenium, rhodium, palladium, silver, osmium, iridium, platinum and gold, and according to other embodiments may also include mercury, rhenium, titanium, niobium and tantalum. In the context of the present invention, according to some embodiments thereof, the group of "noble metals"

includes those metals listed above that can provide catalytic oxidation properties to polyoxometalate complexes.

According to some embodiments of the invention, the noble metal which forms a part of the NM-POM catalytic complex is palladium (Pd). Complexes having palladium as the noble metal, and any hydrate form thereof, are referred to herein as Pd-POM complexes.

The term "solvate" refers to a complex of variable stoichiometry (e.g., di-, tri-, tetra-, penta-, hexa-, and so on up to 1000-), which is formed by a solute (e.g., an NM-POM complex as presented herein) and a solvent, whereby the solvent does not interfere with the activity of the solute. Suitable solvents and solvent mixture may include, for example, water, acetonitrile, ethanol, acetic acid and the like.

The term "hydrate" refers to a solvate, as defined hereinabove, where the solvent is water. The number of water molecules in a hydrate can range from 1 and up to 1,000.

According to some embodiments, the number of noble metal elements in the complex is 2, such that d in Formula I is 2. In exemplary embodiments, the complex comprises 2 Pd atoms.

Whenever d is greater than 1, the noble metal elements can be the same or different. In some embodiments, each of the noble metal elements in the complex is the same.

Similarly, for any of the other variables in the general formula above, in cases where the integer next to the variable is greater than 1, the respective elements can be the same or different.

The phrase "main group element" includes all elements of columns Ina, IVa, Va and VIa of the Periodic Chart of the Elements such as, but not limited to, B, Al, Ga, C, Si, Ge, Sn, Pb, P, As, Sb, Bi, S, Se and Te. In the context of the present embodiments, and according to publications in the field, Zn (zinc) is also considered a main-group element.

As used herein in the specification and claims, the term "alkali metal" includes to Na, K, Li, Rb and Cs. In some embodiments, the alkali metal is Na.

The phrase "alkaline earth metal" includes Ca, Ba, Mg and Sr.

The phrase "transition metal", includes all transition elements of columns Ib to VIIb and VIII of the Periodic Chart of the Elements. Accordingly, X in Formula I above can be, without limitation, Sc, Ti, V, Cr, Mn, Fe, Co, Ni, Cu, Cd, Zn and also noble transition metals such as Ru, Pd, Rh, Ir, Os and Pt.

According to some embodiments of the present invention, X is Zn, Co, P, B, As, Ge, Si, Bi, Al, Sn and/or Sb.

According to some embodiments of the present invention, M is W, Mo and/or V. In some embodiments, M is W and/or Mo.

The term "ligand", as used herein, refers to an atom, an ion, or a molecule (including parts of molecules, namely functional groups) that can bind to a central metal atom in a metal coordination complex such as the noble-metal polyoxometalate complexes. The bonding between the metal and ligand generally involves formal donation of one or more of the ligands electrons, hence the metal-ligand bonding type ranges from covalent to more ionic. Non-limiting examples of ligands include water, iodide, bromide, chloride, fluoride, sulfide (thio, —SH), thiocyanate, nitrate, nitrite, azide, nitrosyl, cyanide (cyano, —CN), carbon monoxide (carbonyl, =C=O), hydroxide (—OH), oxalate, isothiocyanate, acetonitrile, ammonia, ethylenediamine, glycinate, pyrazine, pyridine, 2,2'-bipyridine, 1,10-phenanthroline and triphenylphosphine.

According to some embodiments of the present invention, the ligand may be $H_2O$, halide, oxygen, hydroxyl, DMSO, sulphoxide, cyanide, cyanate, thiocyanate, amine, heteroaryl, heteroalicyclic and any combination thereof. According to other embodiments, the ligand is water ($H_2O$).

According to some embodiments, Q (the counter-cation countering the charge $q^-$) can be any suitable cation including, without limitation, alkali metal cations (such as $Li^+$, $Na^+$, $K^+$, $Rb^+$, $Cs^+$ or $Fr^+$), alkaline earth metal cations (such as $Be^{2+}$, $Mg^{2+}$, $Ca^{2+}$, $Sr^{2+}$, $Ba^{2+}$ or $Ra^{2+}$), transition metal cations (such as cations of Sc, Ti, V, Cr, Mn, Fe, Co, Ni, Cu, Zn, Y, Zr, Nb, Mo, Ru, Rh, Pd, Ag, Cd, Hf, Ta, W, Os, Ir, Pt, Au and Hg), cations of metalloid elements (such as B, Si, Ge, As, Sb, Te and Po), organic cations, substituted or unsubstituted quaternary ammonium cations (such as tricaprylmethyl ammonium), phosphonium cations, and any combination thereof.

According to some embodiments, the counter cation is a quaternary ammonium cation having the general Formula II:

Formula II wherein each of $R_1$, $R_2$, $R_3$ and $R_4$ is independently selected from the group consisting of hydrogen, alkyl, alkenyl, cycloalkyl, heteroalicyclic, aryl and heteroaryl.

According to some embodiments of the present invention, the quaternary ammonium cation is composed of at least one high alkyl, namely at least $R_1$ is alkyl having from 4 to 20 carbon atoms. According to other embodiments $R_2$, $R_3$ and $R_4$ are low alkyls, namely each independently is an alkyl having from 1 to 4 carbon atoms.

According to some embodiments of the present invention, Q is the quaternary ammonium cation $C_{16}H_{33}(CH_3)_3N^+$. Selecting this and other quaternary ammonium cations having high alkyls improves the solubility of the complex in organic solvents.

As indicated hereinabove, the complexes described herein can be in a form of a solvate, e.g., a hydrate. Polyoxometalates in which the counter ion is an alkali metal cation, which are therefore water-soluble, are typically obtained in a form of a hydrate, as defined herein. Complexes in a form a hydrate are formed with water molecules, in addition to water ligands, if present. The number of water molecules in the hydrate can be from 1 to 1,000.

As demonstrated in the Examples section that follows, exceptional results were obtained in selective oxidation of primary alcohols to their corresponding aldehydes, while using an exemplary NM-POM complex having Formula I above and comprising palladium as a noble metal; NM, Zn as X, W as M; $H_2O$ as L; and $C_{16}H_{33}(CH_3)_3N^+$ as Q, and having the formulae:

or also referred to herein as Pd-POM-1.

The exemplary Pd-POM catalysts have shown several unique and notable properties, especially for the aerobic oxidation of saturated aliphatic alcohols, as follows:

(i) a significant preference for the oxidation of primary versus secondary aliphatic alcohols;

(ii) a highly selective oxidation reaction towards aldehyde with little formation of carboxylic acid, namely over-oxidation is inhibited;

(iii) no base is required to activate the alcohol; and (iv) the oxidation reaction is relatively fast, occurring within 15-50 minutes, and in some embodiments from 20-30 minutes.

Without being bound to any particular theory, it is assumed that the fast reaction is related to the electron acceptor nature of the polyoxometalate ligand that presumably facilitates alcohol dehydrogenation and also may lead to catalyst re-oxidation pathway which is atypical for $Pd^{II}$ catalyzed alcohol oxidation.

Without being bound by any particular theory, it is also assumed that a preference for oxidation of primary alcohols is exhibited due to the intrinsically higher probability (more C—H bonds) for oxidation of primary alcohols attenuated by steric factors, namely the NM-POM-mediated/catalyzed oxidation reaction is affected by the 3-dimensional structure of the NM-POM catalyst which offers a narrow cross-section for contact or proximity therewith respect too the reacting alcohols, and thus secondary alcohols, being more sterically hindered at the C-0 bond site, would be less likely to react versus primary alcohols.

The phrase "primary alcohol", as used herein, refers to a compound having at least one —OH group attached to a methylene group, namely, a compound containing a R—CH$_2$—OH group, as oppose to the phrase "secondary alcohol" which refers to a compound containing R—CR'H—OH, or the phrase "tertiary alcohol" which refers to a compound containing R—CR'R"—OH, whereas R, R' and R" can each independently be an alkyl, an alkenyl, an alkynyl, a cycloalkyl, an aryl, a heteroalicyclic or a heteroaryl, as defined herein, each being substituted by various substituents, as defined herein, or unsubstituted.

As used herein, the term "alkyl" describes an aliphatic hydrocarbon including straight chain and branched chain groups. According to some embodiments, the alkyl group has 1 to 20 carbon atoms, and more preferably 1-10 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. As used herein, the term "low alkyl" refers to an alkyl having 1-3 carbon atoms in its main hydrocarbon chain, and the term "high alkyl" refers to an alkyl having 4-20 carbon atoms in its main hydrocarbon chain. The alkyl can be substituted or unsubstituted. When substituted, the substituent can be, for example, an alkyl, an alkenyl, an alkynyl, a cycloalkyl, an aryl, a heteroaryl, a halide, a hydroxyl and an alkoxy, as these terms are defined herein.

The term "alkenyl" describes an unsaturated alkyl, as defined herein, having at least two carbon atoms and at least one carbon-carbon double bond. The alkenyl may be substituted or unsubstituted by one or more substituents, as described herein.

The term "alkynyl", as defined herein, is an unsaturated alkyl having at least two carbon atoms and at least one carbon-carbon triple bond. The alkynyl may be substituted or unsubstituted by one or more substituents, as described herein.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted.

The term "heteroaryl" describes a monocyclic or fused ring (i.e., rings which share an adjacent pair of atoms) group having in the ring(s) one or more atoms, such as, to for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted.

The optional presence of any given substituent at any given position in a compound or group described herein, is subject to the chemical feasibility of such substitution, hence the scope of the present embodiments is meant to span chemical substitutions based on chemical feasibility.

Substituted alkyls, alkenyls, alryls, heteroalicyclics, heteroaryls and the likes may also have other substituents such as, for example, hydroxyl, halo, amine, sulfonate, sulfoxide, phosphonate, alkoxy, aryloxy, thiohydroxy, thioalkoxy, thioaryloxy, cyano, isocyanate, nitro, azo, S/N-sulfonamide, C/O-carboxylate, N/O-thiocarbamate, urea, thiourea, N/O-carbamate, C/N-amide guanyl, guanidine and hydrazine. The number of substituents in each of the groups described herein can vary from null to one, two, three, four, five, six and even more.

The term "hydroxyl" describes a —OH group.

The term "alkoxy" describes both an —O-alkyl and an —O-cycloalkyl group, as defined herein.

The term "amine" is used herein to describe a —NR'R" group, whereas R' and R" are as defined herein.

The term "halide" and "halo" describes fluorine, chlorine, bromine or iodine.

The term "sulfate" describes a —O—S($=$O)$_2$—OR', where R' is as defined hereinabove.

The term "sulfonate" describes a —S($=$O)$_2$—R', where R' is as defined herein.

The term "sulfoxide" or "sulfinyl" describes a —S($=$O)R', where R' is as defined hereinabove.

The term "S-sulfonamide" describes a —S($=$O)$_2$—NR'R", with R' and R" as defined herein.

The term "N-sulfonamide" describes an R'S($=$O)$_2$—NR"—, where R' and R" are as defined herein.

The term "phosphonate" describes a —P($=$O)(OR')(OR"), with R' and R" as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C$\equiv$N group.

The term "isocyanate" describes an —N$=$C$=$O group.

The term "nitro" describes an —NO$_2$ group.

The term "azo" or "diazo" describes an —N$=$NR', with R' as defined hereinabove.

The term "C-carboxylate" describes a —C($=$O)—OR', where R' is as defined herein.

The term "O-carboxylate" describes a —OC($=$O)R', where R' is as defined herein.

The term "C-thiocarboxylate" describes a —C($=$S)—OR', where R' is as defined herein.

The term "O-thiocarboxylate" describes a —OC($=$S)R', where R' is as defined herein.

The term "N-carbamate" describes an R"OC(=O)—NR'—, with R' and R" as defined herein.

The term "O-carbamate" describes an —OC(=O)—NR'R", with R' and R" as defined herein.

The term "O-thiocarbamate" describes a —OC(=S)—NR'R", with R' and R" as defined herein.

The term "N-thiocarbamate" describes an R"OC(=S)NR'—, with R' and R" as defined herein.

The term "S-dithiocarbamate" describes a —SC(=S)—NR'R", with R' and R" as defined herein.

The term "N-dithiocarbamate" describes an R"SC(=S)NR'—, with R' and R" as defined herein.

The term "urea", which is also referred to herein as "ureido", describes a —NR'C(=O)—NR"R'", where R' and R" are as defined herein and R'" is as defined herein for R' and R".

The term "thiourea", which is also referred to herein as "thioureido", describes a —NR'—C(=S)—NR"R'", with R', R" and R'" as defined herein.

The term "C-amide" describes a —C(=O)—NR'R", where R' and R" are as defined herein.

The term "N-amide" describes a R'C(=O)—NR"—, where R' and R" are as defined herein.

The term "guanyl" describes a R'R"NC(=N)—, where R' and R" are as defined herein.

The term "guanidine" describes a —R'NC(=N)—NR"R'", where R', R" and R'" are as defined herein.

The term "hydrazine" describes a —NR'—NR"R'", with R', R", and R'" as defined herein.

According to embodiments of the present invention, primary alcohols which can be subjected to the NM-POM assisted oxidation reaction, include saturated or unsaturated, substituted or unsubstituted aliphatic primary alcohols, saturated or unsaturated, substituted or unsubstituted alicyclic primary alcohols, saturated or unsaturated, substituted or unsubstituted heteroalicyclic primary alcohols, substituted or unsubstituted aromatic primary alcohols and substituted or unsubstituted heteroaryl primary alcohols; all of which can be converted to their corresponding aldehydes.

As used herein, the term "aldehyde" refers to an —C(=O)—H group.

The phrase "corresponding aldehyde", as used herein, refers to the oxidation product of a particular alcohol, wherein the alcohol is a primary alcohol denoted as R—$CH_2$—OH, and thus the corresponding aldehyde is denoted R—CH(=O) and the R group is identical in both R—$CH_2$—OH and R—CH(=O), and is as defined herein.

Similarly, the phrase "corresponding primary alcohol" is referred to herein as a primary alcohol, as defined herein, that is used for synthesizing a particular aldehyde.

The term "corresponding" with respect to aldehydes and alcohols is also referred to herein interchangeably as "respective".

As presented hereinabove, such selective oxidation task is not trivial since (i) primary alcohols are less reactive than secondary alcohols; and (ii) selective oxidation of primary alcohols typically results in over-oxidation of the obtained, relatively unstable, aldehyde to carboxylic acids. Nevertheless, the process according to some embodiments of the present invention, leads to a product mixture wherein the aldehyde, corresponding to the starting primary alcohol, constitutes at least 80 mol percents (yield) of the reaction products. Such a nominal 80% yield is widely accepted as a highly efficient reaction, particularly when considering the alternatives.

According to other embodiments of the invention, the yield of the oxidation reaction of primary alcohols to their respective aldehydes can be more than 85% (mol percents of the total products obtained in the reaction), more than 90%, and more than 95%.

The reaction can be performed in an organic solvent, an aqueous media or a combination thereof, and according to some embodiments, the oxidation reaction is performed in an organic solvent. Suitable organic solvents include chloroform, dichloromethane and other chloro-hydrocarbons, hexane, xylene and other hydrocarbons, acetonitrile, dimethyl sulfoxide, dimethylformamide, dioxane, hexamethylphosphorotriamide, tetrahydrofuran, methylpyrrolidone and other aprotic organic solvents.

As the reaction is based on a regenerative process with respect to the NM-POM, in some embodiments, the reaction is performed in the presence of a catalytic amount of said NM-POM.

The phrase "catalytic amount", is used herein as recognized in the art, and refers to a substoichiometric amount of a catalyst relative to the amount of the reactant(s). As used herein, a catalytic amount is typically in the range from about 0.001 to about 0.1 mole of a NM-POM catalyst per mole of alcohol, namely a ratio of about 1/1000 to about 1/10 catalyst to reactant(s), and in some embodiments the molar ratio ranges from about 1/500 to about 1/10 catalyst to reactant(s), or from about 1/50 to about 1/10 catalyst to reactant(s). In contrast, the phrase "non-catalytic amount", as used herein, refers to a higher ratio of catalyst to reactant(s), namely an amount higher than 0.1 mole of a NM-POM catalyst per mole of alcohol, and up to 0.5 mole, 1 mole (stoichiometric), 1.1 mole and even 1.5 mole and 2 moles of a NM-POM catalyst per mole of alcohol.

The oxidation reaction, according to some embodiments of the present invention, can be performed in the presence or absence of molecular oxygen. According to some embodiments, the oxidation reaction is performed the presence of molecular oxygen, hence in an atmosphere having at least partial pressure of $O_2$. In some embodiments, the oxidation reaction is performed in the presence of a predetermined and controllable partial pressure of $O_2$. According to some embodiments, partial pressure of $O_2$ in the atmosphere at which the reaction is performed ranges from 0.1 bar of $O_2$ to about 5 bar of $O_2$. It is noted herein that the reaction is not limited by its efficiency to 5 bar of $O_2$, however reaction conditions exceeding 5 bar of $O_2$ are considered more hazardous.

The regeneration of the NM-POM complex catalysts presented herein, is linked to the presence of molecular oxygen, namely the rate determining step is assumed to be the $O_2$ dependent re-oxidation step of the catalyst. This step involves the intermediate formation of $H_2O_2$, which is typically decomposed by disproportionation, as illustrated in Scheme 1 hereinabove.

It is therefore noted herein that when the NM-POM complex is used in a catalytic amount, in some embodiments, the presence of at least partial pressure of $O_2$ is required to afford the desired product at notable yields.

Alternatively, the oxidation reaction of primary alcohols to their corresponding aldehydes can be performed in the absence of oxygen, in the presence of a non-catalytic amount of an NM-POM, so as to afford the desired product at notable yields.

According to some embodiments, the oxidation reaction is performed at a temperature that ranges from about 80° C. to about 140° C. However, oxidation reactions performed at higher or lower temperatures are also contemplated.

While searching for noble metals polyoxometalate complexes suitable for performing the above-described process of oxidizing primary alcohols, the present inventors have surprisingly uncovered that such active complexes can be prepared by mixing certain salts of the noble metal with a polyoxometalate, while controlling the ratio of these reactants. The present inventors have uncovered that by selecting the metal salt and controlling the molar ratio thereof with respect to the polyoxometalate, the activity of the resulting complex in the above-described oxidation process can be manipulated.

Hence, according to another aspect of the present invention, there is provided a process of preparing a noble metal-polyoxometalate complex (NM-POM) having the general formula I, as presented hereinabove, which is effected by mixing $NM[(CH_3)_2SO]_2Cl_2$ (NM=noble metal as defined hereinabove and $(CH_3)_2SO$=DMSO) with a solution of a polyoxometalate compound having the general formula III, also referred to herein as the first complex:

Formula III wherein $Q_q$, $X_a$, $L_g$, $M_m$ and $O_z$ are as defined hereinabove for the NM-POM complexes, at a controlled rate and temperature.

The noble-metal/DMSO complex and the first complex are reacted at a molar ratio which ranges from about 10:1 to about 1:10.

In some embodiments, the molar ratio ranges from 5:1 to 1:5, or from 4:1 to 1:4, or from 3:1 to 1:3 or from 2:1 to 1:2. According to some embodiments, the ratio of noble-metal/DMSO salt to the first complex is 1:2.

As presented hereinbelow in the Examples section, the exemplary Pd-POM-1 complex was tested for its aptitude to oxidize alcohols to their corresponding aldehydes, and it was found that a complex obtained using the process described herein, while using 1:2 ratio of $PdCl_2DMSO_2$ to $Q_{12}[Zn_5(H_2O)_2W_{19}O_{68}]$ afforded better results in the catalytic oxidation of alcohols than when the catalyst was prepared from 1:1 $PdCl_2DMSO_2/Q_{12}[Zn_5(H_2O)_2W_{19}O_{68}]$.

It is to be understood that for other complexes, other molar ratios can result in different results, and that the above-mentioned example is presented only for showing the effect of this molar ratio of the activity of the obtained complex. It is within the to capabilities of a person skilled in the art to determine, e.g., via experimentation, a desired molar ratio for obtaining an active complex.

According to embodiments of the present invention, the rate of adding the noble-metal/DMSO complex to the solution of the polyoxometalate compound is drop by drop, so as to allow controlled formation of the desired complex versus undesired side-products.

In some embodiments, the polyoxometalate compound having the general formula III (the first complex) is prepared from another polyoxometalate complex having the general formula IV, also referred to herein as a second complex:

Formula IV and any solvate and hydrate thereof, wherein $X_a$, $L_g$, $M_m$ and $O_z$ are as described hereinabove for the NM-POM complexes; which is reacted with a salt of the desired counter cation (if other than $Na^+$) to thereby replace sodium as the counter cation and obtain the first complex having the general formula III.

An exemplary process by which the NM-POM complexes are afforded is discussed in detail in the Examples section that follows below.

Further according to embodiments of the invention, there are provided noble metal polyoxometalate complexes prepared by the process described herein.

As discussed hereinabove, the process parameters can be manipulated so as to obtain a complex that exhibits a catalytic performance. In some embodiments, the obtained complexes exhibit a desired activity when utilized in a process of oxidizing primary alcohols to their respective aldehyde, as described herein.

According to another aspect of embodiments of the invention there are provided novel NM-POM complexes.

The novel NM-POM complexes according to embodiments of this aspect of the invention can optionally be prepared by the process described herein, such that their structure and/or catalytic activity are controlled by the process parameters. Optionally, to the novel NM-POM complexes described herein share the same chemical features delineated hereinabove for complexes having Formula I as described in detail hereinabove, but are characterized by different structural features.

In some embodiments, the novel NM-POM complexes described herein share the same chemical features delineated hereinabove for complexes having Formula I as described in detail hereinabove, excluding the nature of the variable Q (the counter ion, e.g., cation).

As discussed hereinabove, the nature of the counter ion may affect various properties of the NM-POM complexes, including, for example, solubility.

It is expected that during the life of a patent maturing from this application many relevant noble metal-polyoxometalate complex (NM-POM) catalysts will be developed and the scope of the phrase "noble metal-polyoxometalate complex (NM-POM) catalyst" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Experimental Methods

All oxidation reactions were carried out in 20 ml glass pressure tubes equipped with a pressure valve and a stirring bar. The tubes were loaded with substrate, catalyst and solvent and were gently flushed several times with oxygen. Then the pressure was brought to 2 bars and the reaction vessels were placed in a thermostated oil bath adjusted to appropriate temperature.

Oxidation reaction products were characterized and quantified using reference compounds, when available, using GLC (HP-6890 gas chromatograph) with a flame ionization detector and a 30 m×0.32 mm 5% phenylmethylsilicone (0.25 µm coating) capillary column and helium carrier gas. Products whose initial identities were questionable were identified unambiguously using a gas chromatograph equipped with a mass selective detector (GC-MS HP 5973) and with the same column described above.

IR spectra were recorded on a Nicolet 6700 FTIR spectrometer as KBr pellets.

UV-Visible spectra were recorded on Agilent 89090A spectrophotometer.

$^1$H NMR spectra were measured on a Bruker Avance DPX 500 spectrometer using TMS as external standard.

Kinetic isotope effects were measured in competitive reactions by reacting equimolar concentrations of deuturated and protonated substrates. Peaks were quantified by comparing molecular peak intensities of the starting materials and the oxidized products.

Example 1

Preparation of an Exemplary Pd-POM Catalyst

The preparation of exemplary NM-POM complex catalysts, having palladium(II) and referred to generally as Pd-POM, is presented hereinbelow.

The quaternary ammonium salt of the polyoxometalate, $Q_{12}[Zn_5(H_2O)_2W_{19}O_{68}]$ where $Q=C_{16}H_{33}(CH_3)_3N^+$, was prepared by drop-wise addition of 1 mmol of the parent polyoxometalate, $Na_{12}[Zn_5(H_2O)_2W_{19}O_{68}]\cdot46H_2O$ (prepared as described by Tourné, C. M. et al. in *J. Chem. Soc., Dalton Trans.* 1991, 143-155) dissolved in 10 ml of water, to 12 mmols of $C_{16}H_{33}(CH_3)_3N^+Cl^-$ (25% aqueous solution).

The precipitate which subsequently formed was separated by centrifugation, filtered off and dried overnight under vacuum at 80° C., and thermogravimetric analysis showed no water was present.

Elemental analysis (experimental (calculated) %): C, 33.02 (32.76); H, 6.24 (6.03); N, 1.98 (2.01).

The Pd(II) supported polyoxometalate catalyst was prepared by drop-wise addition of 0.167 grams (0.5 mmol) of $Pd[(CH_3)_2SO]_2Cl_2$ (prepared as described by Price, J. R. et al. in *Inorg. Chem.* 1972, 11, 1280-1284), dissolved in 4 ml of $CH_2Cl_2$, to a solution of 8.36 grams (1 mmol) of $Q_{12}[Zn_5(H_2O)_2W_{19}O_{68}]$ in 50 ml $CH_2Cl_2$ at 35° C. The rate of addition of $Pd[(CH_3)_2SO]_2Cl_2$ was controlled by observation and dissolution of a transient precipitate as the solution turned yellow and then brown.

After stirring the solution for another 10 minutes, the solvent was removed and the residue was dried under vacuum overnight. The resulting brown solid was used as a Pd-POM type catalyst without further purification and has an estimated molecular formula of $(C_{16}H_{33}(CH_3)_3N^+)_{12}[Zn_5(H_2O)_2PdCl_2W_{19}O_{68}]$ wherein Q is the counter cation $C_{16}H_{33}(CH_3)_3N^+$, also referred herein as Pd-POM-1.

Although it has been known that the addition of Pd(II) salts to $Na_{12}[Zn_5(H_2O)_2W_{19}O_{68}]$ in aqueous media typically leads to metathetical substitution of the terminal zinc atoms in the polyoxometalate, such a mixing in an organic solvent did not yield a complex whose structure could be determined unambiguously since the compound obtained could not be purified and analyzed by single crystal X-ray diffraction.

Figure 2:
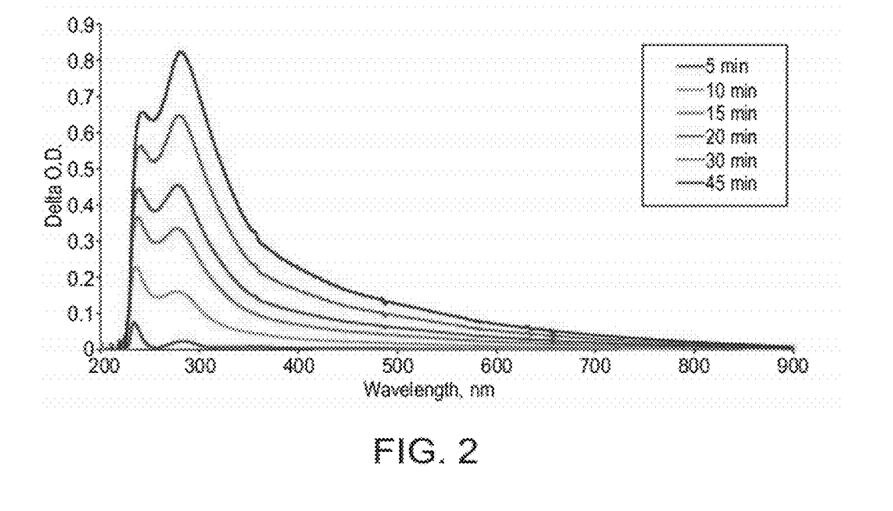
FIG. 2 presents a comparative plot of optical density versus wavelength as observed by following the formation of Pd-POM by UV-vis spectroscopy (difference spectra) in a 0.02 mM solution in $CH_2Cl_2$. As can be seen in FIG. 2, the reaction of $Q_{12}\{[WZn_3(H_2O)_2](ZnW_9O_{34})_2\}$ with $PdCl_2DMSO_2$ was characterized by formation of a brown solution.

FIG. 2 presents a comparative plot of optical density versus wavelength as observed following the formation of Pd-POM by UV-vis spectroscopy (difference spectra) in a 0.02 mM solution in $CH_2Cl_2$. As can be seen in FIG. 2, the reaction of $Q_{12}[Zn_5(H_2O)_2W_{19}O_{68}]$ with $PdCl_2DMSO_2$ was characterized by formation of a brown solution.

$^1$H-NMR measurements indicated that the reaction of $PdCl_2DMSO_2$ with $Q_{12}[Zn_5(H_2O)_2W_{19}O_{68}]$ released free DMSO into solution. Thus, the Pd-POM compound can be formulated as having $Pd^{II}$ incorporated in or supported on the polyoxometalate where oxygen atoms of the polyoxometalate replace the good leaving DMSO ligands of $PdCl_2DMSO_2$; the polyoxometalate acts as a ligand to $Pd^{II}$. Support for such a formulation also comes from the observation that $Q_{12}[Zn_5(H_2O)_2W_{19}O_{68}]$ did not react with Pd(1,10-phenanthroline)$Cl_2$ under similar conditions (1,10-phenanthroline being a stronger coordinating ligand) and no active catalyst was obtained from such a mixture.

Figure 1A:
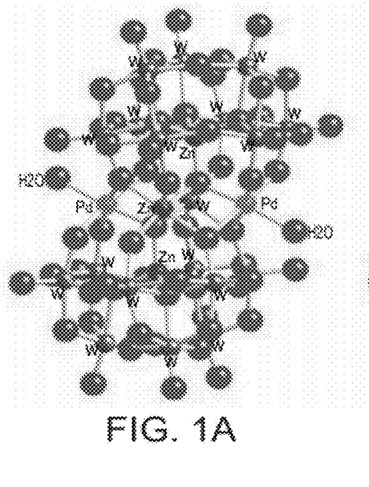
FIGS. 1A-B are two possible schematic representations of an exemplary palladium(II)-polyoxometalate complex (Pd-POM-1) according to some embodiments of the present invention, showing $Pd^{II}$ incorporated at the terminal positions of the polyoxometalate by metathetical substitution (FIG. 1A), and $Pd^{II}$ supported on the surface of the polyoxometalate where the position is arbitrary (FIG. 1B), whereas Zn is represented as purple spheres, W as black spheres, O as red spheres, Pd as green spheres, and L (namely $H_2O$, Cl etc.) as orange spheres.
Figure 1B:
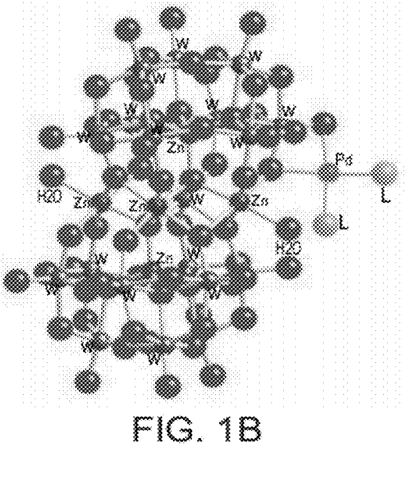

Assumed three-dimensional structures of Pd-POM are illustrated in FIGS. 1A-B, showing an exemplary Pd-POM: —$(C_{16}H_{33}(CH_3)_3N^+)_{12}[Zn_3Pd_2(H_2O)_2W_{19}O_{68}]$ or $(C_{16}H_{33}(CH_3)_3N^+)_{12}[Zn_5(H_2O)_2PdCl_2W_{19}O_{68}]$.

Example 2

Catalytic Oxidation of Primary Alcohols Using Pd-POM Catalyst

The aerobic oxidation of primary alcohols was studied using 1-heptanol as a model substrate. An exemplary reaction was carried out by mixing 0.1 mmol 1-heptanol and 5 μmol of the exemplary Pd-based catalyst Pd-POM-1, in 1 ml of α,α,α-trifluorotoluene (TFT) under 2 bars $O_2$ at 110° C. Typically, after 25-30 minutes a maximum conversion was obtained with high selectivity to n-heptanal. Some minor over-oxidation to n-heptanoic acid and some alcohol oxidation-alkane dehydrogenation to β-unsaturated aldehyde were observed, as can be seen in Scheme 2 below.

Scheme 2

A similar reaction using a catalyst prepared from 1:1 $PdCl_2DMSO_2:Q_{12}[Zn_5(H_2O)_2W_{19}O_{68}]$ showed a 90% conversion of 1-heptanol with 91% selectivity to heptanal, and with formation of 5% heptanoic acid.

Several observations and conclusions were obtained from the above experiment:
  i) No base was needed to commence and complete the reaction;
  ii) neither $Q_{12}[Zn_5(H_2O)_2W_{19}O_{68}]$ nor $PdCl_2DMSO_2$ alone were active catalysts for alcohol oxidation; and
  iii) a reaction under anaerobic conditions (50 μmol 1-heptanol and 5 μmol Pd-POM in 1 ml α,α,α-trifluorotoluene (TFT) under 1 bar of Argon at 110° C.) showed the immediate (within one minute) formation of 2.5 μmol heptanal (5% conversion) consistent with a two-electron oxidation of 1-heptanol by Pd(II).

Figure 3A:
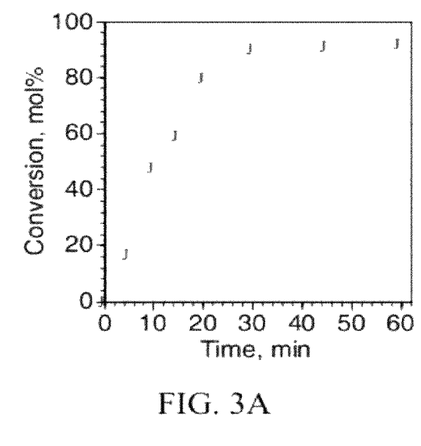
FIGS. 3A-B present plots of reaction progress, showing the reaction profile for the oxidation of 1-heptanol (FIG. 3A) and 2-octanol (FIG. 3B), wherein the reaction conditions included 0.1 mmol of the respective alcohol, 5 μmol of an exemplary Pd-based catalysts Pd-POM, 1 ml TFT, 2 bar O2, and 110° C.
Figure 3B:
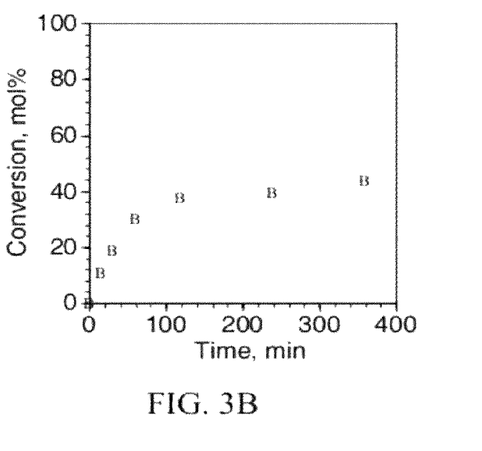

The reaction progress was followed by sampling and GC-analysis, and the results are presented in FIGS. 3A-B.

FIGS. 3A-B present plots of reaction progress, showing the reaction profile for the oxidation of 1-heptanol (FIG. 3A) and 2-octanol (FIG. 3B), wherein the reaction conditions included 0.1 mmol of the respective alcohol, 5 μmol of the exemplary Pd-based catalysts Pd-POM-1, 1 ml TFT, 2 bar O2, and 110° C.

As can be seen in FIGS. 3A-B, the preference for the oxidation of primary versus secondary alcohols catalyzed by Pd-POM-1 is made evident by the reaction profiles of the respective oxidation reaction, were maximal conversion yields of 92% for 1-heptanol (30 minutes) and 44% for 2-octanol (360 minutes) were obtained. The reaction appeared to stop due to deactivation of the catalyst through formation of palladium black, a phenomenon which is known and documented for other palladium-based catalysts.

The results for the aerobic oxidation of various additional primary and secondary alcohols to their respective aldehydes and ketones, under reaction conditions of 0.1 mmol alcohol, 5 µmol Pd-POM-1, 1 ml TFT, 2 bar $O_2$, and 110° C., are presented in Table 1 below.

Table 1 presents the results of the oxidation reaction based on GC analysis as molar percentage. The by-products were identified as β-unsaturated aldehyde and carboxylic acid formed in similar amounts. The level of selectivity is presented as molar percentage of all products.

TABLE 1

| Alcohol | Primary Alcohol % Oxidation (% Selectivity) | Secondary Alcohol % Oxidation (% Selectivity) |
|---|---|---|
| $C_4H_9OH$ | 65 (99) | 3 (>99) |
| $C_6H_{13}OH$ | 88 (95) | 27 (>99) |
| $C_7H_{15}OH$ | 92 (94) | 23 (>99) |
| $C_8H_{17}OH$ | 89 (91) | 31 (>99) |
| $C_9H_{19}OH$ | 89 (88) | 24 (>99) |
| $C_{10}H_{21}OH$ | 81 (89) | 27 (>99) |
| c-$C_6H_{11}OH$ | | 34 (>99) |
| c-$C_8H_{15}OH$ | | 58 (>99) |

As can be seen in Table 1, the results show a similar profile as presented in Scheme 2 for primary alcohols. Corresponding secondary alcohols were oxidized to ketones in essentially 100% selectivity. Shorter chain alcohols tended to oxidize at significantly lower yields.

The regiospecificity of the aliphatic alcohol oxidation reactions was also manifested in the comparative conversion observed using four octanol isomers as substrates. Thus, 1-octanol, 2-ethyl-1-hexanol, 2-octanol, and 3-octanol showed conversion of 89, 76, 21 and 15 molar percentages, respectively, after 30 minutes (0.1 mmol alcohol, 5 µmol Pd-POM-1, 1 ml TFT, 2 bar $O_2$, and 110° C.), demonstrating both the preferred reactivity of primary over secondary alcohols, as well as additional preferred reactivity of less hindered alcohols, namely 1-octanol>2-ethyl-1-hexanol and 2-octanol>3-octanol.

Expectedly, benzylic alcohols such as $PhCH_2OH$, 4-$CH_3OPhCH_2OH$, 4-$CF_3PhCH_2OH$, and $PhCHOHCH_3$ were also reactive (0.1 mmol substrate, 5 µmol Pd-POM-1, 1 ml TFT, 2 bar $O_2$, and 110° C. for 20 minutes), all yielding the corresponding benzaldehyde derivatives or acetophenone with >95% yields with no observed by-products.

In the oxidation reaction of unsaturated aliphatic alcohols, the maximal oxidation rates obtained for secondary alcohols was higher than those observed for primary alcohols, as presented in Table 2. The only significant by-products in these reactions were the saturated aldehdyes or ketones, namely propanal, hexanal, butanone and so forth, and in the cases where the alcohols were pure E/Z hexen-1-ol isomers, the E-2-hexenal was the major product. No significant amounts of carboxylic acids were formed.

Table 2 presents the results obtained for unsaturated alcohols under reaction conditions of 0.1 mmol alcohol, 5 µmol Pd-POM-1, 1 ml TFT, 2 bars $O_2$, and 110° C., wherein the rate of oxidation yields, determined by GC analysis, is shown as molar percentage, the time for completion/arrest in minutes, and the selectivity for the major product (β-unsaturated aldehyde or ketone respectively) in molar percentage.

TABLE 2

| Alcohol | % of oxidation yield (time of reaction in minutes) | % selectivity |
|---|---|---|
| 2-propen-1-ol | 95 (15) | 55 |
| 2-Me-2-propen-1-ol | 42 (25) | 96 |
| E-2-hexen-1-ol | 44 (30) | 93 E-2-hexenal |
| Z-2-hexen-1-ol | 21 (30) | 91 E-2-hexenal |
| Z-3-hexen-1-ol | 28 (30) | 99 E-2-hexenal |
| 1-buten-3-ol | 74 (25) | 80 |
| cyclohexen-3-ol | 74 (30) | 86 |
| 1-octen-3-ol | 93 (30) | 88 |

As can be seen in Table 2, the cis isomers were isomerized to trans products, to and as noticeable from the formation of saturated aldehydes and ketones as by-products, the isomerisation of the double bond competed with the alcohol oxidation reaction.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A process of oxidizing a primary alcohol to a corresponding aldehyde, the process comprising mixing the primary alcohol with a noble metal-polyoxometalate complex (NM-POM), thereby obtaining the aldehyde, wherein the noble metal is selected from the group consisting of palladium and platinum.

2. The process of claim 1, wherein the aldehyde constitutes at least 80 mol percents of the products obtained upon said mixing.

3. The process of claim 1, wherein the aldehyde constitutes at least 90 mol percents of the products obtained upon said mixing.

4. The process of claim 1, wherein said noble metal-polyoxometalate complex (NM-POM) has a general Formula I:

Formula I and any solvate and hydrate thereof, wherein:

X is a heteroatom selected from the group consisting of a main group element, H, alkali metal, alkaline earth metal, a transition metal or any combination thereof;

a is 0 or an integer from 1 to 6;

NM is said noble metal selected from the group consisting of palladium and platinum;

d is an integer from 1 to 10;

L is a ligand selected from the group consisting of $H_2O$, halide, oxygen, hydroxyl, DMSO, sulphoxide, cyanide, cyanate, thiocyanate, amine, heteroaryl, heteroalicyclic and any combination thereof;

g an integer from 1 to 10;

M is selected from the group consisting of tungsten (W), molybdenum (Mo), niobium (Nb) or vanadium (V) or any combination thereof;

m is an integer from 4 to 100;

O is oxygen;

z in an integer from 5 to 400;

Q is a counter-cation selected from the group consisting of an alkali metal cation, an alkaline earth metal cation, a transition metal cation, an organic cation, a substituted or unsubstituted quaternary ammonium cation, a phosphonium cation, an arsenium cation and any combination thereof; and q is an integer from 1 to 100.

5. The process of claim 4, wherein d is 2.

6. The process of claim 4, wherein said quaternary ammonium cation has a general Formula II:

$(R_1R_2R_3R_4)N^+$  Formula II wherein each of $R_1$, $R_2$, $R_3$ and $R_4$ is independently selected from the group consisting of hydrogen, alkyl, alkenyl, cycloalkyl, heteroalicyclic, aryl and heteroaryl.

7. The process of claim 4, wherein said noble metal-polyoxometalate complex is $(C_{16}H_{33}(CH_3)_3N^+)_{12}[Zn_3Pd_2(H_2O)_2W_{19}O_{68}]$.

8. A process of oxidizing a primary alcohol to a corresponding aldehyde, the process comprising mixing the primary alcohol with a noble metal-polyoxometalate complex (NM-POM), thereby obtaining the aldehyde, wherein the aldehyde constitutes at least 80 mol percents of the products obtained upon said mixing.

9. The process of claim 8, wherein the aldehyde constitutes at least 85 mol percents of the products obtained upon said mixing.

10. The process of claim 8, wherein the aldehyde constitutes at least 90 mol percents of the products obtained upon said mixing.

11. The process of claim 8, wherein said mixing is performed in the presence of a catalytic amount of said NM-POM.

12. The process of claim 8, wherein said mixing is effected in an atmosphere having an $O_2$ partial pressure.

13. The process of claim 12, wherein said $O_2$ partial pressure ranges from 0.1 bar to about 5 bar.

14. The process of claim 8, wherein said mixing is effected in the absence of $O_2$.

15. The process of claim 14, wherein said mixing is performed in the presence of a non-catalytic amount of said NM-POM.

16. The process of claim 8, wherein the primary alcohol is selected from the group consisting of a saturated or unsaturated, substituted or unsubstituted aliphatic alcohol, a saturated or unsaturated, substituted or unsubstituted alicyclic alcohol, a saturated or unsaturated, substituted or unsubstituted heteroalicyclic alcohol, a substituted or unsubstituted aromatic alcohol and a substituted or unsubstituted heteroaromatic alcohol.

17. The process of claim 5, wherein said noble metal-polyoxometalate complex (NM-POM) has a general Formula I:

$Q^+_q[X_a(NM)_dL_gM_mO_z]^{q-}$  Formula I and any solvate and hydrate thereof, wherein:

X is a heteroatom selected from the group consisting of a main group element, H, alkali metal, alkaline earth metal, a transition metal or any combination thereof;

a is 0 or an integer from 1 to 6;

NM is a noble metal selected from the group consisting of palladium, ruthenium, rhodium, silver, osmium, iridium, platinum and gold;

d is an integer from 1 to 10;

L is a ligand selected from the group consisting of $H_2O$, halide, oxygen, hydroxyl, DMSO, sulphoxide, cyanide, cyanate, thiocyanate, amine, heteroaryl, heteroalicyclic and any combination thereof;

g an integer from 1 to 10;

M is selected from the group consisting of tungsten (W), molybdenum (Mo), niobium (Nb) or vanadium (V) or any combination thereof;

m is an integer from 4 to 100;

O is oxygen;

z in an integer from 5 to 400;

Q is a counter-cation selected from the group consisting of an alkali metal cation, an alkaline earth metal cation, a transition metal cation, an organic cation, a substituted or unsubstituted quaternary ammonium cation, a phosphonium cation, an arsenium cation and any combination thereof; and q is an integer from 1 to 100.

18. The process of claim 17, wherein said noble metal (NM) is palladium.

19. The process of claim 18, wherein d is 2.

20. The process of claim 17, wherein said quaternary ammonium cation has a general Formula II:

$(R_1R_2R_3R_4)N^+$  Formula II wherein each of $R_1$, $R_2$, $R_3$ and $R_4$ is independently selected from the group consisting of hydrogen, alkyl, alkenyl, cycloalkyl, heteroalicyclic, aryl and heteroaryl.

21. The process of claim 20, wherein said quaternary ammonium cation is $C_{16}H_{33}(CH_3)_3N^+$.

22. The process of claim 17, wherein X is selected from the group consisting of Zn, Co, P, B, As, Ge, Si, Bi, Al, Sn and Sb.

23. The process of claim 17, wherein M is selected from the group consisting of W, Mo and V.

24. The process of claim 17, wherein L is $H_2O$.

25. The process of claim 17, wherein said noble metal-polyoxometalate complex is $(C_{16}H_{33}(CH_3)_3N^+)_{12}[Zn_3Pd_2(H_2O)_2W_{19}O_{68}]$.

26. A process of preparing a noble metal-polyoxometalate complex (NM-POM) having a general Formula I:

$Q^+_q[X_a(NM)_dL_gM_mO_z]^{q-}$  Formula I and any solvate and hydrate thereof, wherein:

X is selected from the group consisting of a main group element, H, alkali metal, alkaline earth metal, a transition metal or any combination thereof;

a is 0 or an integer from 1 to 6;

NM is a noble metal selected from the group consisting of palladium, ruthenium, rhodium, silver, osmium, iridium, platinum and gold;

d is an integer from 1 to 10;

L is a ligand selected from the group consisting of $H_2O$, halide, oxygen, hydroxyl, DMSO, sulphoxide, cyanide, cyanate, thiocyanate, amine, heteroaryl, heteroalicyclic and any combination thereof;

g an integer from 1 to 10;

M is selected from the group consisting of tungsten (W), molybdenum (Mo), niobium (Nb) or vanadium (V) or any combination thereof;

m is an integer from 4 to 100;
O is oxygen;
z in an integer from 5 to 400;
Q is a counter-cation selected from the group consisting of an alkali metal cation, an alkaline earth metal cation, a transition metal cation, an organic cation, a substituted or unsubstituted quaternary ammonium cation, a phosphonium cation, an arsenium cation and any combination thereof; and
q is an integer from 1 to 100,
the process comprising:
mixing an $NM[(CH_3)_2SO]_2Cl_2$ salt with a solution of a first complex having the general formula III:

$$Q_q[X_aL_gM_mO_z]^{q-} \qquad \text{Formula III}$$

thereby obtaining the NM-POM complex.

27. The process of claim 26, wherein a molar ratio of $NM[(CH_3)_2SO]_2Cl_2$ to said first complex ranges from 3:1 to 1:3.

28. The process of claim 26, wherein said ratio is 1:2.

29. The process of claim 26, wherein said mixing comprises adding $NM[(CH_3)_2SO]_2Cl_2$ to said solution of said first complex.

30. The process of claim 26, further comprising prior to said mixing:

reacting a second complex having the general formula IV:

$$Na_q[X_aL_gM_mO_z]^{q-} \qquad \text{Formula IV}$$

and any solvate and hydrate thereof,
with a salt having said counter cation to thereby obtain said first complex having the general formula III.

31. The process of claim 26, wherein said counter cation is a quaternary ammonium cation having a general Formula II:

$$(R_1R_2R_3R_4)N^+ \qquad \text{Formula II}$$

wherein each of $R_1$, $R_2$, $R_3$ and $R_4$ is independently selected from the group consisting of hydrogen, alkyl, alkenyl, cycloalkyl, heteroalicyclic, aryl and heteroaryl.

32. The process of claim 26, wherein NM is palladium.

33. The process of claim 26, wherein X is selected from the group consisting of Zn, Co, P, B, As, Ge, Si, Bi, Al, Sn and Sb.

34. The process of claim 26, wherein M is selected from the group consisting of W, Mo and V.

35. The process of claim 26, wherein L is $H_2O$.

36. The process of claim 26, wherein said noble metal-polyoxometalate complex is $(C_{16}H_{33}(CH_3)_3N^+)_{12}[Zn_5(H_2O)_2PdCl_2W_{19}O_{68}]$.

37. A noble metal-polyoxometalate complex being $(C_{16}H_{33}(CH_3)_3N^+)_{12}[Zn_5(H_2O)_2PdCl_2W_{19}O_{68}]$.

* * * * *